US009125854B2

(12) United States Patent
Bottje et al.

(10) Patent No.: US 9,125,854 B2
(45) Date of Patent: *Sep. 8, 2015

(54) COMPOSITIONS AND METHODS OF ENHANCING IMMUNE RESPONSES TO FLAGELLATED BACTERIUM

(75) Inventors: Walter Bottje, Fayetteville, AR (US); Billy Hargis, Fayetteville, AR (US); Luc Berghman, College Station, TX (US); Young Min Kwon, Springdale, AR (US); Kimberly Cole, Raymond, OH (US); Mandy Cox, Fayetteville, AR (US); Sherryll Layton, Fayetteville, AR (US)

(73) Assignees: The Board of Trustees of the University of Arkansas, Little Rock, AR (US); The Texas A&M University System, College Station, TX (US)

( * ) Notice: Subject to any disclaimer, the term of this patent is extended or adjusted under 35 U.S.C. 154(b) by 1241 days.

This patent is subject to a terminal disclaimer.

(21) Appl. No.: 12/740,631

(22) PCT Filed: Oct. 30, 2008
(Under 37 CFR 1.47)

(86) PCT No.: PCT/US2008/081813
§ 371 (c)(1),
(2), (4) Date: Jan. 7, 2011

(87) PCT Pub. No.: WO2009/059018
PCT Pub. Date: May 7, 2009

(65) Prior Publication Data
US 2011/0159026 A1 Jun. 30, 2011

Related U.S. Application Data

(60) Provisional application No. 60/983,803, filed on Oct. 30, 2007.

(51) Int. Cl.
*A61K 39/02* (2006.01)
*A61K 39/112* (2006.01)
*A61K 39/00* (2006.01)

(52) U.S. Cl.
CPC ....... *A61K 39/0275* (2013.01); *A61K 2039/522* (2013.01); *A61K 2039/552* (2013.01)

(58) Field of Classification Search
None
See application file for complete search history.

(56) References Cited

U.S. PATENT DOCUMENTS

| | | | |
|---|---|---|---|
| 5,683,700 A | 11/1997 | Charles et al. | |
| 5,747,309 A | 5/1998 | Allan et al. | |
| 5,962,406 A | 10/1999 | Armitage et al. | |
| 5,981,724 A | 11/1999 | Armitage et al. | |
| 6,087,329 A | 7/2000 | Armitage et al. | |
| 6,190,669 B1 | 2/2001 | Noriega et al. | |
| 6,248,329 B1* | 6/2001 | Chandrashekar et al. | 424/191.1 |
| 6,264,951 B1 | 7/2001 | Armitage et al. | |
| 6,290,972 B1 | 9/2001 | Armitage et al. | |
| 6,306,387 B1 | 10/2001 | Galan | |
| 6,410,711 B1 | 6/2002 | Armitage et al. | |
| 6,479,258 B1 | 11/2002 | Short | |
| 6,713,279 B1 | 3/2004 | Short | |
| 6,902,906 B1 | 6/2005 | Chatfield | |
| 6,923,957 B2 | 8/2005 | Lowery et al. | |
| 6,923,958 B2 | 8/2005 | Xiang et al. | |
| 6,936,425 B1 | 8/2005 | Hensel et al. | |
| 6,969,609 B1 | 11/2005 | Schlom et al. | |
| 7,087,573 B1 | 8/2006 | Lazarus et al. | |
| 7,332,298 B2 | 2/2008 | Kornbluth | |
| 7,371,392 B2 | 5/2008 | Tripp et al. | |
| 7,405,270 B2 | 7/2008 | Armitage et al. | |
| 7,495,090 B2 | 2/2009 | Prussak et al. | |
| 7,842,501 B2 | 11/2010 | Cai et al. | |
| 7,928,213 B2 | 4/2011 | Prussak et al. | |
| 8,604,178 B2* | 12/2013 | Bottje et al. | 536/23.7 |
| 2001/0021386 A1 | 9/2001 | Nuijten et al. | |
| 2004/0006006 A9 | 1/2004 | Armitage et al. | |
| 2004/0047873 A1 | 3/2004 | Al-Shamkhani et al. | |
| 2004/0203039 A1 | 10/2004 | Hensel et al. | |
| 2005/0147627 A1 | 7/2005 | Aderem et al. | |
| 2005/0181994 A1 | 8/2005 | Chamberlain et al. | |
| 2005/0226888 A1 | 10/2005 | Deisseroth et al. | |
| 2006/0014248 A1 | 1/2006 | Marshall et al. | |
| 2006/0078994 A1 | 4/2006 | Healey et al. | |
| 2006/0233829 A1* | 10/2006 | Curtiss | 424/200.1 |
| 2006/0286074 A1 | 12/2006 | Tang et al. | |
| 2007/0025982 A1 | 2/2007 | Ledbetter et al. | |

(Continued)

FOREIGN PATENT DOCUMENTS

| WO | WO 93/08207 | 4/1993 |
|---|---|---|
| WO | WO 95/14487 | 6/1995 |

(Continued)

OTHER PUBLICATIONS

Al-Ramadi et al 2005 The American Association of Immunologist pp. 496-506.*
Bowie et al (Science, 1990, 247:1306-1310).*
McSorley et al 2000 The Journal of Immunology 2000 164: pp. 986-993.*
Greenspan et al (Nature Biotechnology 7: 936-937, 1999).*
Skolnick et al. (Trends in Biotech., 18(1 ):34-39, 2000).*
Vega et al (Immunology, 110:206-216, 2003).*
Andersen-Nissen et al PNAS, 102(26):9247-9252, 2005).*
Andersen-Nissen et al (JEM, 204(2):393-403, Feb. 19, 2007).*
Agterberg, M. et al., "Outer membrane protein PhoE as a carrier for the exposure of foreign antigenic determinants at the bacterial cell surface," Antoine Van Leeuwenhoek (1991) 59(4):249-262.

(Continued)

*Primary Examiner* — Patricia A Duffy
(74) *Attorney, Agent, or Firm* — Andrus Intellectual Property Law, LLP

(57) ABSTRACT

Vaccines comprising fliC and CD154 polypeptides and *Salmonella enteritidis* vaccine vectors comprising fliC polypeptides are provided. Also provided are methods of enhancing an immune response against flagellated bacteria and methods of reducing morbidity associated with infection with flagellated bacteria.

18 Claims, 4 Drawing Sheets

(56) References Cited

U.S. PATENT DOCUMENTS

| | | |
|---|---|---|
| 2007/0082400 A1 | 4/2007 | Healey et al. |
| 2007/0128183 A1 | 6/2007 | Meinke et al. |
| 2007/0128223 A1 | 6/2007 | Tang et al. |
| 2007/0237779 A1* | 10/2007 | Ledbetter et al. .......... 424/155.1 |
| 2009/0004194 A1 | 1/2009 | Kedl |
| 2010/0047231 A1 | 2/2010 | Zabaleta Azpiroz et al. |
| 2010/0112002 A1 | 5/2010 | Lien et al. |
| 2010/0291109 A1 | 11/2010 | Kedl |
| 2010/0292309 A1 | 11/2010 | Vile et al. |

FOREIGN PATENT DOCUMENTS

| | | |
|---|---|---|
| WO | WO 96/26735 | 9/1996 |
| WO | WO 96/40918 | 12/1996 |
| WO | WO 99/27948 | 6/1999 |
| WO | WO 99/32138 | 7/1999 |
| WO | WO 00/63395 | 10/2000 |
| WO | WO 00/63405 | 10/2000 |
| WO | WO 01/42298 | 6/2001 |
| WO | WO 01/56602 | 8/2001 |
| WO | WO 02/36769 | 5/2002 |
| WO | WO 02/092773 | 11/2002 |
| WO | WO 03/099340 | 12/2003 |
| WO | WO 2004/009615 | 1/2004 |
| WO | WO 2005/035570 | 4/2005 |
| WO | WO 2005/058950 | 6/2005 |
| WO | WO 2005/113598 | 12/2005 |
| WO | WO 2006/042177 | 4/2006 |
| WO | WO 2006/105972 | 10/2006 |
| WO | WO 2007/042583 | 4/2007 |
| WO | WO 2007/054658 | 5/2007 |
| WO | WO 2007/056266 | 5/2007 |
| WO | WO 2007/103048 | 9/2007 |
| WO | WO 2007/117682 | 10/2007 |
| WO | WO 2008/036675 | 3/2008 |
| WO | WO 2008/109825 | 9/2008 |
| WO | WO 2009/059298 | 5/2009 |

OTHER PUBLICATIONS

Barr, T.A. et al., "A potent adjuvant effect of CD40 antibody attached to antigen," Immunology (2003) 109:87-92.
Barrow, P. A., et al., "Reduction in faecal excretion of *Salmonella typhimurium* strain F98 in chickens vaccinated with live and killed *S. typhimurium* organisms," Epidemiol. Infect. (1990) 104:413-426.
Blomfield, I.C. et al., "Allelic exchange in *Escherichia coli* using the *Bacillus subtilis* sacB gene and a temperature-sensitive pSC101 replicon," Mol Microbiol (1991) 5(6):1447-1457.
Charbit, A. et al., "Probing the topology of a bacterial membrane protein by genetic insertion of a foreign epitope; expression at the cell surface," EMBO J (1986) 5(11):3029-3037.
Charbit, A. et al., "Versality of a vector for expressing foregin polypeptides at the surface of gram-negative bacteria," Gene (1988) 70(1):181-189.
Cole, K. et al., "Evaluation of a novel recombinant *Salmonella* vaccine vector for avian influenza," Poultry Science 92007) 86(Suppl. 1):585-586.
Cox, M.M. et al., "Scarless and site-directed mutagenesis in *Salmonella enteritidis* chromosome," BMC Biotech. (2007) 7(59):10 pages.
Farnell, M.B. et al., "Upregulation of oxidative burst and degranulation in chicken heterophils stimulated with probiotic bacteria," Poult. Sci. (2006) 85:1900-1906.
Fecteau, J.F, et al., "CD40 Stimulation of Human Peripheral B Lymphocytes: Distinct Response from Naïve and Memory Cells," J Immunol (2003) 171:4621-4629.
Gares, S.L. et al., "Immunotargeting with CD154 (CD40 ligand) enhances DNA vaccine responses in ducks," Clin. Vaccine Immun. (2006) 13:958-965.
Gast, R.K. et al., "The relationship between the magnitude of the specific antibody response to experimental *Salmonella enteritidis* infection in laying hens and their production of contaminated eggs," Avain Diseases (2001) 45:425-431.
Grangette, C. et al., Protection against tetanus toxin after intragastric adminstration of two recombinant lactic acid bacteria: Impact and strain viability and in vivo persistence, Vaccine (2002) 20:3304-3309.
Grewal, L.S. et al., "CD40 and CD154 in cell-mediated immunity," Annu. Rev. Immunology. (1998) 16:111-135.
Harcourt, J.L. et al., "CD40 ligand (CD154) improves the durability of respiratory syneytial virus DNA vaccination in BALB/c mice," Vaccine (2003) 21(21-22):2964-2979.
Hayes, L.J. et al., "*Chlamydia trachomatis* major outer membrane protein epitopes expressed as fusions with LamB in an attenuated aro A strain of *Salmonella typhimurium*; their application as potential immunogens," J. of General Microbiology (1991) 137:1557-1564.
Holmgren, J. et al., "Mucosal immunity: implications for vaccine development," Immunobiol. (1992) 184:157-179.
Husseiny, M.L. et al., "Rapid method for the construction of *Salmonella enterica* serovar typhimurium vaccine carrier strains," Infec. Immun. (2005) 73(3):1598-1605.
Kajikawa, A et al., "Intragastric immunization with recombinant *Lactobaccillus casei* expressing flagellar antigen confers antibody-independent protective immunity against *Salmonella enterica* serovar Enteritidis," Vaccine (2007) 25(18):3599-3605.
Katz, J.M. et al., "Adjuvant activity of the heat-labile enterotoxin from enterotoxigenic *Escherichia coli* for oral adminstration of inactivated influenza virus vaccine," J. Infect. Dis. (1997) 175:352-363.
Koch, F. et al., "High level IL-12 production by murine dendritic cells: upregulation via MHC class II and CD40 molecules and downregulation by IL-4 and IL-10," J. Exp. Med. (1996) 184:741-746.
Kotton, C.N. et al., "Enteric pathogens as vaccine vectors for foreign antigen delivery," Infect. Immun. (2004) 72:5535-5547.
Kwon, Y.M. et al., "*Salmonella*-based vaccines for infections diseases," Expert Review of Vaccines (2007) 6(2):147-152.
Lapalombella, R. et al., "A Novel Raji-Burkitt's Lymphoma Model for Preclinical and Mechanistic Evaluation of CD52-Targeted Immunotherapeutic Agents," Clin. Cancer Res. (2008) 14:569-578.
Lee, J.S. et al., "Surface-displayed viral antigens on *Salmonella* carrier vaccine," Nat. Biotechnol. (2000) 18:645-648.
Li, W., "Synergistic antibody induction by antigen-CD40 ligand fusion protein as improved immunogen," Immunology (2005) 11(2):215-222.
Lowe, D.C. et al., "Characterization of candidate live oral *Salmonella typhi* vaccine strains harboring defined mutations in aroA, aroC, and htrA," Infection and Immunity Feb. 1999:700-707.
Miga, A. et al., "The role of CD40-CD154 interactions in the regulation of cell mediated immunity," Immunol. Invest. (2000) 29:111-114.
O'Callaghan, D. et al., "Immunogenicity of foreing peptide epitopes expressed in bacterial envelope proteins," Research in Microbiology (1990) 141:963-969.
Passeti, M. et al., "Animal modes paving the way for clinical trials of attenuated *Salmonella enterica* servoar Typhi live oral vaccines and live vectors," V accine (2003) 21:401-418.
Rabsch, W. et al., "Competitive exclusion of *Salmonella enteritidis* by *Salmonella* gallinarum in poultry," Emerging Inf. Diseases (2000) 6(5):443-448.
Russmann, H. et al., "Delivery of epitopes by the salmonella type III secretion system for vaccines development," Science (1998) 281(5376):565-568.
Su, G.F. et al., "Construction of stable LamB-Shiga toxin B subunit hybrids: analysis of expression in *Salmonella typhimurium* aroA strains and stimulation of B subunit-specific mucosal and serum antibody responses," Infect Immun (1992) 60(8):3345-3359.
Tregaskes, C.A. et al., "Conservation of biological properties of the CD40 ligand, CD154 in a non-mammalian vertebrate," Dev. Comp. Immunol. (2005) 29:361-374.
Vega, M.L. et al., "A *Salmonella typhi* OmpC fusion protein expressing the CD154 Trp140-Ser149 amino acid strand binds CD40 and activates a lymphoma B-cell line," Immunol. (2003) 110:206-216.

(56) References Cited

OTHER PUBLICATIONS

Verjans, G.M. et al., "Intracellular processing and presentation of T Cell epitopes, expressed by recombinant *Escherichia coli* and *Salmonella typhimurium*, to human T cells," Eur J Immunol (1995) 25(2):405-410.

Vierira-Pinto, M. et al., "Occurrence of *Salmonella* in the ileum, ileocolic lymph nodes, tonsils, mandibular lymph nodes and carcasses of pigs slaughtered for consumption," J Vet Med B Infection Dis Vet Public Health (2005) 52(10):476-481.

Wang, J. et al., "Immunogenicity of viral B-cell epitopes inserted into two surface loops of the *Escherichia coli* K12 LamB protein and expressed in an attenuated aroA strain of *Salmonella typhimurium*," Vaccine (1999) 17(1):1-12.

Xu, Y. et al., "The role of CD40-CD154 interaction in cell immunoregulation," J. Biomed. Sci. (2004) 11:426-438.

Babu, U., et al, "*Salmonella enteritidis* clearance and immune responses in chickens following *Salmonella* vaccination and challenge," Vet. Immunol. Immunopathol. (2004)101:251-257.

Chatfield et al., "The development of oral vaccines based on live attenuated *Salmonella* strains," FEMS Immunol. Med. Microbiol. (1993) 7:1-7.

Fernandez-Cabezudo et al., "Evidence for the requirement for CD40-CD154 interactions in resistance to infections with attenuated *Salmonella*," J. Endotoxin Res. (2005) 11:395-399.

Lavelle, E.C. et al., "Delivery systems and adjuvants for oral vaccines," Expert Opin. Drug Deliv. (2006) 3(6):747-762.

Mohamadzadeh, M. et al., "Targeting mucosal dendritic cells with microbial antigens from probiotic lactic acid bacteria," Expert Rev. Vaccines (2008) 7(2):163-174 (Abstract).

Moyle, P.M. et al.. "Mucosal immunisation: adjuvants and delivery systems," Curr. Drug Deliv. (2004) 1(4):385-396 (Abstract).

Swayne, D,E., "Vaccines for List A poultry diseases: emphasis on avian influenza," Dev. Biol. (2003) 114:201-212.

International Search Report and Written Opinion for Application No. PCT/US08/81813 dated May 12, 2009 (13 pages).

Examination Report for European Patent Application No. 08 832 781.2 dated Jan. 9, 2013 (5 pages).

Manoj, S. et al., "Targeting with Bovine CD154 enhances humoral immune responses induced by a DNA vaccine in sheep," (2003) Journal of Immunology 170:989-996.

Nakajima, A. et al., "Antitumor effect of CD40 ligand: Elicitation of local and systemic antitumor responses by IL-12 and B7," (1998) Journal of Immunology 161:1901-1907.

Ochoa-Reparaz, J. et al., "Humoral immune response in hens naturally infected with *Salmonella entertidis* against outer membrane proteins and other surface structural antigens," (2004) Vet. Res. 35:291-298.

\* cited by examiner

PCR-A

PCR-B

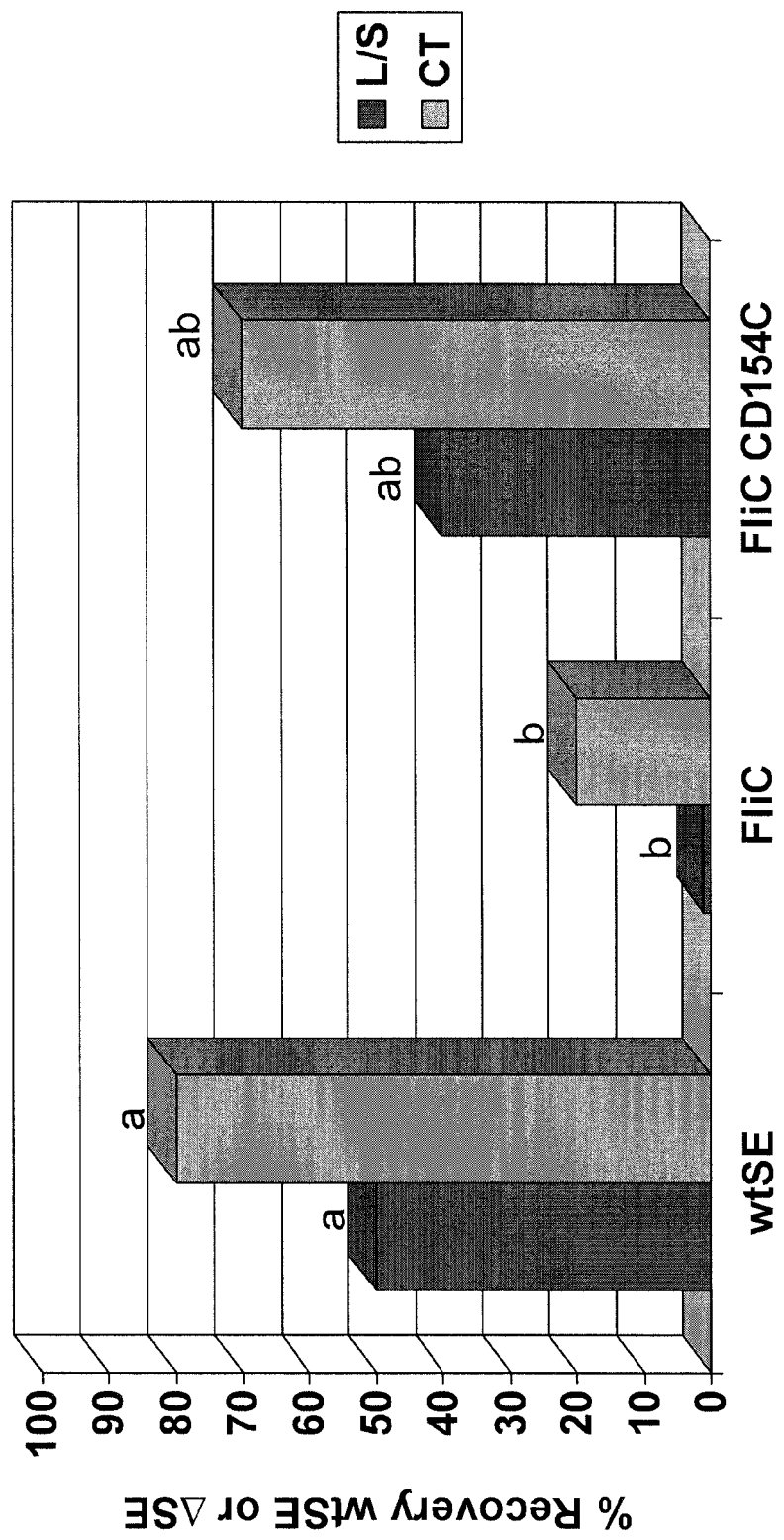

COMPOSITIONS AND METHODS OF ENHANCING IMMUNE RESPONSES TO FLAGELLATED BACTERIUM

CROSS-REFERENCE TO RELATED APPLICATIONS

This application is a national stage filing under 35 U.S.C. 371 of International Application No. PCT/US2008/081813, filed Oct. 30, 2008, which claims priority to U.S. Provisional Application Ser. No. 60/983,803, filed Oct. 30, 2007, both of which are incorporated herein by reference in their entirety.

STATEMENT REGARDING FEDERALLY SPONSORED RESEARCH

This invention was made with partial United States government support awarded by USDA/NRI Proposal #2007-01953. The United States may have certain rights in this invention.

INTRODUCTION

*Salmonella* continues to be one of the most commonly reported bacterial causes of human food-borne infections worldwide, and epidemiological evidence indicates that poultry and poultry products are a significant source of human infection. In the United States, an estimated 1.4 million cases of human Salmonellosis are reported annually. Of these cases, *S. enterica* serovars Enteritidis (SE) and Typhimurium (ST) are the most commonly isolated, although a number of other serovars have also been shown to cause enteritis in humans.

*Salmonella* infrequently causes apparent clinical disease in poultry flocks. However, infection in young chicks with some *Salmonella* isolates results in 2% mortality within the first 48 hours post-hatch, and up to 20% morbidity within the first five days. Therefore, increasing the resistance of the poultry population against *Salmonella* will not only reduce the impact of low level disease on performance, but will also reduce the significant health risk for the human population as well.

SUMMARY

A vaccine comprising a fliC polynucleotide sequence encoding a first polypeptide and a second polynucleotide sequence encoding a CD154 polypeptide is disclosed. The CD154 polypeptide is capable of binding CD40 and has fewer than 50 amino acids, and includes amino acids 140-149 of SEQ ID NO: 8 or a homolog thereof.

In another aspect, a vaccine comprising a variant of *Salmonella enteritidis* 13A is disclosed. The *Salmonella* comprises a first polynucleotide sequence encoding a fliC polypeptide.

In yet another aspect, methods of enhancing the immune response against a flagellated bacterium in a subject by administering a bacterium are provided. The bacterium includes a first polynucleotide sequence encoding a fliC polypeptide and a second polynucleotide sequence encoding a CD154 polypeptide. The CD154 polypeptide is capable of binding CD40 and has fewer than 50 amino acids, and includes amino acids 140-149 of SEQ ID NO: 8 or a homolog thereof. The bacterium is administered in an amount effective to enhance the immune response of the subject to the flagellated bacterium.

In still another aspect, methods of enhancing the immune response against a flagellated bacterium in a subject by administering a variant of *Salmonella enteritidis* 13A are provided. The *Salmonella* includes a first polynucleotide sequence encoding a fliC polypeptide. The *Salmonella* is administered in an amount effective to enhance the immune response of the subject to the flagellated bacterium.

In a still further aspect, methods of reducing morbidity associated with infection with a flagellated bacterium in a subject by administering a bacterium are provided. The bacterium includes a first polynucleotide sequence encoding a fliC polypeptide and a second polynucleotide sequence encoding a CD154 polypeptide. The CD154 polypeptide is capable of binding CD40, and has fewer than 50 amino acids, and includes amino acids 140-149 of SEQ ID NO: 8 or a homolog thereof. The bacterium is administered in an amount effective to reduce the morbidity of the subject after infection with the flagellated bacterium.

In another aspect, methods of reducing the morbidity of infection with a flagellated bacterium in a subject by administering a variant of *Salmonella enteritidis* 13A are provided. The *Salmonella* includes a first polynucleotide sequence encoding a fliC polypeptide. The *Salmonella* is administered in an amount effective to reduce the morbidity of the subject after infection with the flagellated bacterium.

BRIEF DESCRIPTION OF THE DRAWINGS

FIG. 4 is a bar graph showing the percent *Salmonella enteritidis* recovery as compared to the initial inoculum in the liver/spleen and cecal tonsils at 21 days post-inoculation with the indicated bacteria.

DETAILED DESCRIPTION

Figure 1:
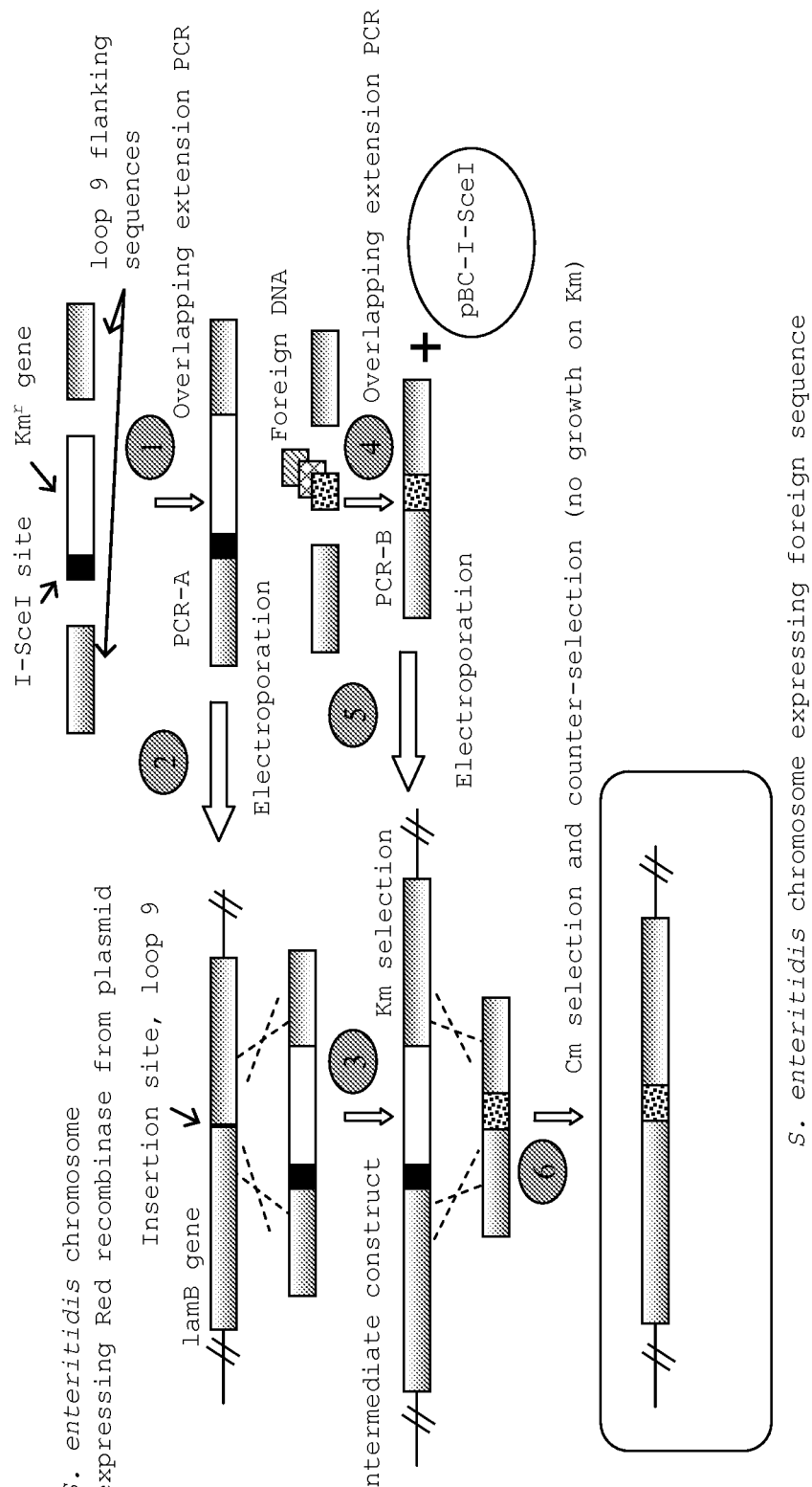
FIG. 1 depicts the scheme for making site-directed mutations in *Salmonella enteritidis*.

Vaccination against *Salmonella* is difficult because over 2,000 serovars have been described and immunity to one serovar generally does not confer immunity to a distinct serovar. Development of a vaccine to protect humans, poultry and other domesticated animals from Salmonellosis is needed. A vaccine capable of protecting against multiple serovars would be optimal. A vaccine comprising a highly conserved region of fliC, a flagellar filament protein found on flagellated *Salmonella*, is provided.

Recombinant DNA technologies enable relatively easy manipulation of many bacterial and viral species. Some bacteria and viruses are mildly pathogenic or non-pathogenic, but are capable of generating a robust immune response. These bacteria and viruses make attractive vaccine vectors for eliciting an immune response to antigens. Bacterial or viral vaccine vectors may mimic a natural infection and produce robust and long lasting immunity. Vaccine vectors are often relatively inexpensive to produce and administer. In addition, such vectors can often carry more than one antigen and may provide protection against multiple infectious agents.

In one aspect, a vaccine comprising a first polynucleotide sequence encoding a fliC polypeptide and a second polynucleotide sequence encoding a CD154 polypeptide which is capable of binding CD40 is provided. In another aspect, the use of vaccine vectors, such as bacterial vectors, for vaccination and generation of immune responses against *Salmonella* and other flagellated pathogenic bacteria is disclosed. *Salmonella* strains make suitable vaccine vectors because bacterial genes may be mutated or attenuated to create bacteria with low to no pathogenesis to the infected or immunized subject, while maintaining immunogenicity.

The majority of *Salmonella* isolates contain two genes that encode flagellar (H) antigens, fliC and fljB, which are alternately expressed by a phase-variation mechanism. The phase 1 antigens are encoded by fliC whereas fljB encodes the phase 2 antigens. A conserved region within fliC that has almost 100% homology between multiple *Salmonella* serovars and between fliC and fljB has been identified. This conserved region of fliC is depicted in SEQ ID NO: 1 and was used to generate several vaccine vectors as described in the Examples. Other possible polypeptides for use in vaccine vectors are disclosed in SEQ ID NO: 2 (a similar region of fliC from *E. coli*), SEQ ID NO: 10, SEQ ID NO: 11 or SEQ ID NO: 12. Immunogenic fragments of the fliC polypeptides may also be used to generate vaccines. In addition, there is extensive homology between this conserved region of fliC and flagellar sequences of other bacteria, such as *Shigella* and *E. coli*, such that a vaccine vector expressing fliC may enhance the immune response to flagellated bacteria generally. Therefore, expression of these protective epitopes on the surface of a *Salmonella* vaccine vector may induce protective immunity against multiple serovars of the organism and may allow immunization against all flagellated bacterium.

Involvement of dendritic cells (DCs) is essential for the initiation of a powerful immune response as they possess the unique ability to activate naïve T cells, causing T cell expansion and differentiation into effector cells. It is the role of the DC, which is an antigen presenting cell (APC) found in virtually all tissues of the body, to capture antigens, transport them to associated lymphoid tissue, and then present them to naïve T cells. Upon activation by DCs, T cells expand, differentiate into effector cells, leave the secondary immune organs, and enter peripheral tissues. Activated cytotoxic T cells (CTLs) are able to destroy virus-infected cells, tumor cells or even APCs infected with intracellular parasites (e.g., *Salmonella*) and have been shown to be critical in the protection against viral infection.

CD40 is a member of the TNF-receptor family of molecules and is expressed on a variety of cell types, including professional antigen-presenting cells (APCs), such as DCs and B cells. Interaction of CD40 with its ligand CD154 is extremely important and stimulatory for both humoral and cellular immunity. Stimulation of DCs via CD40, expressed on the surface of DCs, can be simulated by anti-CD40 antibodies. In the body, however, this occurs by interaction with the natural ligand for CD40 (i.e. CD154) expressed on the surface of activated T-cells. Interestingly, the CD40-binding regions of CD154 have been identified. The CD40-binding region of CD154 may be expressed on the surface of a vaccine vector, such as a *Salmonella* vaccine vector, and may result in an enhanced immune response against a co-presented peptide sequence.

*Salmonella* can survive the gastrointestinal tract of the host and give rise to a mucosal immune response. Oral vaccines using a *Salmonella* vector produce a robust mucosal immune response and are relatively easy to administer to both animals and humans. However, many of the current attenuated *Salmonella* vaccine strains are not as effective in generating a strong protective immune response as compared to their more virulent counterparts. Virulent strains provide a robust immune response but may also cause significant morbidity to the vaccinated subject. A *Salmonella* strain that could be used for effective mucosal, e.g., oral, vaccination would provide a vector that could be used to readily vaccinate a subject against one or more pathogenic agents, such as flagellated bacteria. Alternatively, a method of limiting an infection caused by a *Salmonella* vaccine vector would also be useful. Provided herein are methods of limiting an infection caused by a *Salmonella* vaccine vector by administering the *Salmonella* vaccine vector to a subject and administering a second vaccine vector comprising a first polynucleotide sequence encoding a fliC polypeptide. Administration of the second vaccine vector enhances the immune response to *Salmonella* and limits the infection caused by the *Salmonella* vaccine vector. The second vaccine vector may be administered before, at the same time as or after the *Salmonella* vaccine vector.

A *Salmonella enteritidis* strain useful as a vaccine vector, and various recombinant vaccine vectors made using this strain, are described. Specifically, a *Salmonella enteritidis* 13A (SE13A) capable of expressing an exogenous fliC polypeptide is provided. In addition, a vaccine vector and methods of enhancing an immune response in a subject by administering the vaccine vector comprising a first polynucleotide sequence encoding a fliC polypeptide and a second polynucleotide sequence encoding a polypeptide of CD154 or a homolog thereof that is capable of binding to CD40 are disclosed. The vaccine vectors may be used to enhance an immune response against *Salmonella* or another flagellated bacterium, such as *Escherichia coli* or *Shigella*, or may be used to reduce the morbidity associated with a flagellated bacterial infection.

A wild-type isolate of *Salmonella*, *Salmonella enteritidis* 13A (SE13A) (deposited with the American Type Culture Collection (ATCC) on Sep. 13, 2006, deposit number PTA-7871), was selected based upon its unusual ability to cause mucosal colonization and submucosal translocation in chickens, permitting robust presentation of associated antigens or epitopes in commercial chickens. Importantly, this wild-type *Salmonella* isolate causes no clinically detectable disease or loss of performance in commercial chickens, indicating little disease-causing potential of the wild-type *Salmonella* in vertebrate animals.

The SE13A isolate may be further attenuated by inactivating at least one gene necessary for sustained replication of the bacteria outside of laboratory or manufacturing conditions. Attenuated or variant *Salmonella* strains that can be used as vaccine vectors are described below. SE13A was used to generate attenuated *Salmonella* strains to develop vaccines and generate enhanced immune responses. SE13A is invasive, non-pathogenic for poultry and causes no measurable morbidity. These features result in an enhanced immune response as compared to non-invasive bacterial vectors. Attenuation of SE13A by mutation of genes that limit the ability of the bacterium to spread may increase the safety of the vaccine. For example, SE13A strains with mutations in aroA and/or htrA retain the ability to generate an immune response, but have limited replication in the host. Thus, the attenuation increases the safety of the vaccine vector without compromising the immunogenicity.

Mutations may be made in a variety of other *Salmonella* genes including, but not limited to, cya, crp, asd, cdt, phoP, phoQ, ompR, outer membrane proteins, dam, htrA or other stress related genes, aro, pur and gua. As shown in the Examples, mutations in aroA and htrA were found to attenuate SE13A. The aro genes are enzymes involved in the shikimate biosynthesis pathway or the aromatase pathway and aro mutants are auxotrophic for the aromatic amino acids tryptophan, tyrosine and phenylalanine htrA is a stress response gene that encodes a periplasmic protease that degrades aberrant proteins. Mutants in htrA are also attenuated and display increased sensitivity to hydrogen peroxide.

The mutations in aroA and htrA described in the Examples are deletion mutations, but the mutations can be made in a variety of ways. Suitably, the mutations are non-reverting mutations that cannot be repaired in a single step. Suitable mutations include deletions, inversions, insertions and substitutions. A vaccine vector may include more than one mutation, for example a vaccine vector may contain mutations in both aroA and htrA. Methods of making such mutations are well known in the art.

SE13A or the attenuated SE13A variants may be used as vaccine vectors. Polynucleotides encoding fliC polypeptide antigens and other antigens from any number of pathogenic organisms may be inserted into the bacteria and expressed by the bacteria to generate antigenic polypeptides. The polynucleotides may be inserted into the chromosome of the bacteria or encoded on plasmids or other extrachromosomal DNA. Suitably, polynucleotides encoding fliC antigens are inserted into a bacterial polynucleotide that is expressed. Suitably, the bacterial polynucleotide encodes a transmembrane protein, and the polynucleotide encoding the fliC antigen is inserted into the bacterial polynucleotide sequence to allow expression of the fliC antigen on the surface of the bacteria. For example, the polynucleotide encoding fliC may be inserted in frame into the bacterial polynucleotide in a region encoding an external loop region of a transmembrane protein such that the bacterial polynucleotide sequence remains in frame. See Example 1.

Alternatively, the first polynucleotide encoding fliC antigen may be inserted into a polynucleotide encoding a secreted polypeptide. Those of skill in the art will appreciate that the polynucleotide encoding the fliC antigen could be inserted in a wide variety of bacterial polynucleotides to provide expression and presentation of the fliC antigen to the immune cells of a subject treated with the bacterial vaccine vector. In the Examples, a polynucleotide encoding a fliC antigen was inserted into loop 9 of the lamB gene of SE13A. The polynucleotide encoding the fliC antigen may be included in a single copy or more than one copy. In the Examples, a bacterial vaccine vector containing a single copy of the fliC antigen inserted into loop 9 of lamB is described. Alternatively, copies of an epitope may be inserted into the bacterial vaccine vector at more than one location. The copies of the polynucleotide may be linked together or separated by a linker. Suitable linkers are known to those of skill in the art and include, but are not limited to a repeated amino acid, such as 1-10 serine residues.

As described in more detail below, a vaccine vector may include a CD154 polypeptide that is capable of binding CD40 in the subject and stimulating the subject to respond to the vaccine vector and its associated antigen. As described above, these polynucleotides may be inserted into the chromosome of the vaccine vector or maintained extrachromosomally. One of skill in the art will appreciate that these polynucleotides can be inserted in a variety of endogenous polynucleotides and expressed in different parts of the vaccine vector such as the cell wall or may be secreted. The polynucleotide encoding a CD154 polypeptide capable of enhancing the immune response to a foreign antigen may also encode the foreign antigen. The polynucleotide encoding a CD154 polypeptide may be linked to the polynucleotide encoding the fliC antigen, such that in the vaccine vector the CD154 polypeptide and the fliC antigen are present on the same polynucleotide. In the Examples, a polynucleotide encoding a polypeptide of CD154 that is capable of binding to CD40 also encodes the fliC antigen. See SEQ ID NOS: 1, 2, 9, 10 and 11 in the attached sequence listing. In the Examples, the polynucleotide encoding the fliC antigen and the polynucleotide encoding the CD154 polypeptide are both inserted in loop 9 of the lamB gene. Those of skill in the art will appreciate that bacterial polynucleotides encoding other transmembrane proteins and other loops of the lamB gene may also be used.

The SE13A bacteria include an exogenous polynucleotide encoding a fliC polypeptide that is a portion of the full-length fliC polypeptide natively associated with *Salmonella*. Suitably a polynucleotide encoding a portion of the fliC polypeptide or the entire fliC polypeptide may be inserted into the vaccine vector. In the Examples, a seven amino acid polypeptide (SEQ ID NO:1) was incorporated into SE13A. Suitably, the portion of the fliC polypeptide inserted into the vaccine vector is an immunogenic fragment. An immunogenic fragment is a peptide or polypeptide capable of eliciting a cellular or humoral immune response. Suitably, an immunogenic fragment of fliC may be 6 or more amino acids, 10 or more amino acids, 15 or more amino acids or 20 or more amino acids of the full-length protein sequence.

Other suitable epitopes for inclusion in a fliC vaccine vector include, but are not limited to, polynucleotides encoding other bacterial polypeptides. One of skill in the art will appreciate that a variety of sequences may be used in combination with any other antigen and may also be used in conjunction with polypeptides encoding immune stimulatory peptides such as a polypeptide of CD154.

As discussed above, a polynucleotide encoding a CD154 polypeptide that is capable of enhancing the immune response to the antigen may be included in the vaccine vector. Suitably, the CD154 polypeptide is fewer than 50 amino acids long, more suitably fewer than 40, fewer than 30 or fewer than 20 amino acids in length. The polypeptide may be between 10 and 15 amino acids, between 10 and 20 amino acids or between 10 and 25 amino acids in length. The CD154 sequence and CD40 binding region are not highly conserved among the various species. The CD154 amino acid sequences of chicken and human are provided in SEQ ID NO: 9 and SEQ ID NO: 8, respectively.

The CD40 binding regions of CD154 have been determined for a number of species, including human, chicken, duck, mouse and cattle and are shown in SEQ ID NO: 3, SEQ ID NO: 4, SEQ ID NO:5, SEQ ID NO:6, SEQ ID NO:7, respectively. Although there is variability in the sequences in the CD40 binding region between species, the human CD154 polypeptide was able to enhance the immune response in chickens. Therefore, one may practice the invention using species specific CD154 polypeptides or a heterologous CD154 polypeptide.

In the Examples, several SE13A recombinant bacteria were generated. In each of the SE13A strains containing polynucleotides encoding both the fliC and CD154 peptides, the fliC polypepetide and the CD154 polypeptide were encoded on the same polynucleotide and were in frame with each other and with the *Salmonella* lamB polynucleotide in which they were inserted. In alternative embodiments, the CD 154 polypeptide and the fliC polypeptide may be encoded by distinct polynucleotides. SE13A aroA htrA fliC contains a deletion in aroA and htrA and encodes both the fliC epitope (SEQ ID NO:1) and optionally the CD154 polypeptide (SEQ ID NO: 3) inserted into loop 9 of lamB.

Compositions comprising an attenuated *Salmonella* strain and a pharmaceutically acceptable carrier are also provided. A pharmaceutically acceptable carrier is any carrier suitable for in vivo administration. Examples of pharmaceutically acceptable carriers suitable for use in the composition include, but are not limited to, water, buffered solutions, glucose solutions or bacterial culture fluids. Additional components of the compositions may suitably include, for example, excipients such as stabilizers, preservatives, diluents, emulsifiers and lubricants. Examples of pharmaceutically acceptable carriers or diluents include stabilizers such as carbohydrates (e.g., sorbitol, mannitol, starch, sucrose, glucose, dextran), proteins such as albumin or casein, protein-containing agents such as bovine serum or skimmed milk and buffers (e.g., phosphate buffer). Especially when such stabilizers are added to the compositions, the composition is suitable for freeze-drying or spray-drying.

Methods of enhancing immune responses in a subject by administering a vaccine vector containing a fliC polypeptide and a CD154 polypeptide capable of binding to CD40 and activating CD40 are also provided. The vaccine vector comprising the polynucleotide encoding a CD154 polypeptide capable of binding to CD40 is administered to a subject in an amount effective to enhance the immune response of the subject to the vaccine. Suitably, the vaccine vector contains a polynucleotide encoding a polypeptide including amino acids 140-149 of the human CD154 polypeptide (SEQ ID NO: 8) or a homolog thereof. As noted above and demonstrated in the Examples, the CD40 binding region of CD154 is not conserved among species, yet heterologous CD154 was capable of enhancing the immune response (i.e. human sequence used in a chicken). Therefore, a homologue of amino acid 140-149 derived from one species may be used to stimulate an immune response in a distinct species.

Several suitable polypeptides are identified herein. Suitably, the polynucleotide encodes a CD154 polypeptide from the same species as the subject. Suitably, a polynucleotide encoding the polypeptide of SEQ ID NO: 3 is used in human subjects, a polynucleotide encoding the polypeptide of SEQ ID NO: 4 is used in chickens, a polynucleotide encoding the polypeptide of SEQ ID NO: 5 is used in ducks, a polynucleotide encoding the polypeptide of SEQ ID NO: 6 is used in mice, and a polynucleotide encoding the polypeptide of SEQ ID NO: 7 is used in cows. In the Examples, the human CD154 polypeptide (SEQ ID NO: 3) was used in a chicken vaccine vector and was demonstrated to enhance the immune response to a foreign antigen. Thus other heterologous combinations of CD154 polypeptides and subjects may be useful in the methods of the invention. The CD154 polypeptide may be used to enhance the immune response in the subject to any foreign antigen or antigenic polypeptide present in the vaccine vector in addition to the fliC polypeptide. One of skill in the art will appreciate that the CD154 polypeptide could be used to enhance the immune response to more than one antigenic polypeptide present in a vaccine vector.

The polypeptide from CD154 stimulates an immune response at least in part by binding to its receptor, CD40. The Examples used a polypeptide homologous to the CD154 polypeptide which is expressed on immune cells of the subject and which is capable of binding to the CD40 receptor on macrophages and other antigen presenting cells. Binding of this ligand-receptor complex stimulates macrophage (and macrophage lineage cells such as dendritic cells) to enhance phagocytosis and antigen presentation while increasing cytokine secretions known to activate other local immune cells (such as B-lymphocytes). As such, molecules associated with the CD154 peptide are preferentially targeted for immune response and expanded antibody production.

Potential vaccine vectors for use in the methods include, but are not limited to, *Salmonella* (*Salmonella enteritidis*), *Shigella, Escherichia* (*E. coli*), *Yersinia, Bordetella, Lactococcus, Lactobacillus, Bacillus, Streptococcus, Vibrio* (*Vibrio cholerae*), *Listeria,* adenovirus, poxvirus, herpesvirus, alphavirus, and adeno-associated virus.

In addition, methods of enhancing an immune response against flagellated bacteria and methods of reducing morbidity associated with subsequent infection with a flagellated bacterium are disclosed. Briefly, the methods comprise administering to a subject a vaccine vector comprising a polynucleotide sequence encoding a fliC polypeptide in an effective amount. The fliC polypeptides include SEQ ID NO:1-2 and 10-12. The insertion of the fliC polypeptides into the vaccine vector may be accomplished in a variety of ways known to those of skill in the art, including but not limited to, the scarless site-directed mutation system described in BMC Biotechnol. 2007 Sep. 17: 7(1): 59, Scarless and Site-directed Mutagenesis in *Salmonella enteritidis* chromosome, which is incorporated herein by reference in its entirety. The vaccine vector may also be engineered to express the fliC polypeptides in conjunction with polynucleotides capable of enhancing the immune response as discussed above, such as in SEQ ID NO:8 and SEQ ID NO:9. In particular, a polypeptide of CD154 capable of binding CD40 may be expressed by the vaccine vector to enhance the immune response of the subject to the fliC polypeptide. Optionally, the vaccine vector is a bacterium, such as *Salmonella enteritidis.*

The useful dosage of the vaccine vector to be administered will vary depending on the age, weight and species of the subject, the mode and route of administration and the type of pathogen against which an immune response is sought. The composition may be administered in any dose sufficient to evoke an immune response. For bacterial vaccines, it is envisioned that doses ranging from $10^3$ to $10^{10}$ bacteria, from $10^4$ to $10^9$ bacteria, or from $10^5$ to $10^7$ bacteria are suitable. The composition may be administered only once or may be administered two or more times to increase the immune response. For example, the composition may be administered two or more times separated by one week, two weeks, or by three or more weeks. The bacteria are suitably viable prior to administration, but in some embodiments the bacteria may be killed prior to administration. In some embodiments, the bacteria may be able to replicate in the subject, while in other embodiments the bacteria may not be capable of replicating in the subject.

For administration to animals or humans, the compositions may be administered by a variety of means including, but not limited to, intranasally, mucosally, by spraying, intradermally, parenterally, subcutaneously, orally, by aerosol, or intramuscularly. Eye-drop administration or addition to drinking water or food are additionally suitable. For chickens, the compositions may be administered in ovo.

Some embodiments of the invention provide methods of enhancing immune responses in a subject. Suitable subjects may include, but are not limited to, vertebrates, suitably mammals, suitably a human, and birds, suitably poultry such as chickens. Other animal models of infection may also be used. Enhancing an immune response includes, but is not limited to, inducing a therapeutic or prophylactic effect that is mediated by the immune system of the subject. Specifically, enhancing an immune response may include enhanced production of antibodies, enhanced class switching of antibody heavy chains, maturation of antigen presenting cells, stimulation of helper T cells, stimulation of cytolytic T cells or induction of T and B cell memory.

It is envisioned that several epitopes or antigens from the same or different pathogens may be administered in combination in a single vaccine vector to generate an enhanced immune response against multiple antigens. Recombinant vaccine vectors may encode antigens from multiple pathogenic microorganisms, viruses or tumor associated antigens. Administration of vaccine vectors capable of expressing multiple antigens has the advantage of inducing immunity against two or more diseases at the same time. For example, live attenuated bacteria, such as *Salmonella enteritidis* 13A, provide a suitable vaccine vector for eliciting an immune response against multiple antigens.

Bacterial vaccines may be constructed using exogenous polynucleotides encoding antigens which may be inserted into the bacterial genome at any non-essential site or alternatively may be carried on a plasmid using methods well known in the art. One suitable site for insertion of polynucleotides is within external portions of transmembrane proteins or coupled to sequences that target the exogenous polynucleotide for secretory pathways. One example of a suitable transmembrane protein for insertion of polynucleotides is the lamB gene. In the Examples, fliC and CD154 polynucleotides were inserted into loop 9 of the lamB sequence.

Exogenous polynucleotides include, but are not limited to, polynucleotides encoding antigens selected from pathogenic microorganisms or viruses and include polynucleotides of the vaccine vector which are expressed in such a way that an effective immune response is generated. Such polynucleotides may be derived from pathogenic viruses such as influenza (e.g., M2e, hemagglutinin, or neuraminidase), herpesviruses (e.g., the genes encoding the structural proteins of herpesviruses), retroviruses (e.g., the gp160 envelope protein), adenoviruses, paramyxoviruses, coronaviruses and the like. Exogenous polynucleotides can also be obtained from pathogenic bacteria, e.g., genes encoding bacterial proteins such as toxins, and outer membrane proteins. Further, exogenous polynucleotides from parasites are attractive candidates for use of a vector vaccine.

Polynucleotides encoding polypeptides involved in triggering the immune system may also be included in a vaccine vector, such as a live attenuated *Salmonella* vaccine. The polynucleotides may encode immune system molecules known for their stimulatory effects, such as an interleukin, Tumor Necrosis Factor, or an interferon, or another polynucleotide involved in immune-regulation. The vaccine vector may also include polynucleotides encoding peptides known to stimulate an immune response, such as the CD154 polypeptide described herein.

The following examples are meant only to be illustrative and are not meant as limitations on the scope of the invention or of the appended claims.

EXAMPLES

Example 1

Construction of fliC and fliC/CD154 Inserts

Strains and Culture Conditions

All plasmids were first maintained in TOP10 *E. coli* cells (Invitrogen, Carlsbad, Calif., USA) unless described otherwise. *Salmonella enteritidis* 13A was used for introduction of mutations. *Salmonella enteritidis* strain 13A was a field isolate available from USDA/APHIS/NVSL and deposited with the ATCC as deposit number PTA-7871. Bacteria carrying plasmid pKD46 were grown at 30° C. Other bacteria were grown at 37° C. Plasmid curing was conducted at 37° C.

Luria-Bertani (LB) media was used for routine growth of cells, and SOC media (Invitrogen, Carlsbad, Calif., USA) was used for phenotypic expression after electroporation. When appropriate, the following antibiotics were added to the media: ampicillin (Amp) at 100 µg/ml, kanamycin (Km) at 50 µg/ml, and chloramphenicol (Cm) at 25 µg/ml.

Plasmids

Plasmids pKD46, pKD13, and pBC-I-SceI were described previously (Datsenko and Wanner, PNAS 2000, 97:6640-6645 and Kang et al., J Bacteriol 2004, 186:4921-4930, both of which are incorporated herein by reference in their entireties). Plasmid pKD46 encodes Red recombinase enzymes which mediate homologous recombination of incoming linear DNA with chromosomal DNA. This plasmid also contains the Ampicillin resistance gene and is temperature-sensitive so that it requires 30° C. for maintenance in the cell. Plasmid pKD13 served as a template for amplification of the Km resistance (Km$^r$) gene used in overlapping PCR. Plasmid pBC-I-SceI, which is maintained in the cell at 37° C., produces the I-SceI enzyme, which cleaves the following 18 base pair, rare recognition sequence: 5'-TAGGGATAACAGGG-TAAT-3' (SEQ ID NO:13). Plasmid pBC-I-SceI also contains the chloramphenicol resistance (Cm$^r$) gene.

PCR

All primers used for PCR are listed in Table 1. Typically, PCR was performed using approximately 0.1 µg of purified genomic, plasmid or PCR-generated DNA (Qiagen, Valencia, Calif., USA), 1× cloned Pfu polymerase buffer, 5U Pfu polymerase (Stratagene La Jolla, Calif., USA), 1 mM dNTPs (GE Healthcare Bio-Sciences Corp., Piscataway, N.J.), and 1.2 µM of each primer in a total volume of 50 µL. The DNA engine thermal cycler (Bio-Rad, Hercules, Calif., USA) was used with the following amplification conditions: 94° C. for 2 minutes; 30 cycles of 94° C. sec for 30 sec, 58° C. for 60 sec, 72° C. for 90 sec per 1 kb; and 72° C. for 10 minutes for final extension. Each PCR product was gel purified (Qiagen, Valencia, Calif., USA) and either eluted in 25 µL EB buffer for preparation of templates used in overlapping extension PCR or in 50 µL EB buffer, ethanol precipitated and suspended in 5 µL of ddH$_2$O for electroporation into *S. enteritidis*.

TABLE 1

| Primer sequences | | |
|---|---|---|
| Primer | Amplified region | Primer sequence |
| lam-up-f | loop 9 up | 5'TGTACAAGTGGACGCCAATC 3' (SEQ ID NO: 14) |
| lam-up-f | | 5'*GTTATCGCCGTCTTTGATATAGCC* 3' (SEQ ID NO: 15) |
| lam-dn-f | 1000p 9 dn | 5'*ATTTCCCGTTATGCCGCAGC* 3' (SEQ ID NO: 16) |
| lam-dn-f | | 5'GTTAAACAGAGGGCGACGAG 3' (SEQ ID NO: 17) |

TABLE 1-continued

Primer sequences

| Primer | Amplified region | Primer sequence |
| --- | --- | --- |
| Km-f | I-SceI/Km^r gene | 5' *GCTATATCAAAGACGGCGATAAC*TAACTATAAC GGTCCTAAGGTAGCGAATTTCCGGGGATCCGTC GA 3' (SEQ ID NO: 18) |
| Km-r | | 5' *GCTGCGGCATAACGGGAAA*TTGTAGGCTGGAGC TGCTTCG 3' (SEQ ID NO: 19) |
| Kan4f | inside Km^r gene: sequencing | 5'CAAAAGCGCTCTGAAGTTCC 3' (SEQ ID NO: 20) |
| Kan4r | | 5'GCGTGAGGGGATCTTGAAGT 3' (SEQ ID NO: 21) |
| fliC up reverse | fliC/loop 9 up | 5'CGGTTCTGTACGGAGGAGGAG*TTATCGCCGTCT TTGATATAGCC* 3' (SEQ ID NO: 22 |
| fliC down forward | fliC/loop 9 down | 5'TCCTCCTCCGTACAGAACCGTTTCAACTCCGCTA TTACCAACCTGGGCAACACCTCCTCCTCCATTTCC *CGTTATGCCGCAGC* 3' (SEQ ID NO: 23) |
| fliC hCD154 up reverse | fliC-hCD154/loop 9 up | 5'GGAGGTGTTGCCCAGGTTGGTAATAGCGGAGTT GAAACGGTTCTGTACGGAGGAGGAG*TTATCGCCG TCTTTGATATAGCC* 3' (SEQ ID NO: 24) |
| fliC hCD154 up reverse | fliC-hCD154/loop 9 down | 5'CCAACCTGGGCAACACCTCCTCCTCCTGGGCAG AAAAAGGTTATTATACCATGTCTTCCTCCTCCATT *TCCCGTTATGCCGCAGC* 3' (SEQ ID NO: 25) |
| fliC cCD154 up reverse | fliC-cCD154/loop 9 up | 5'GGAGGTGTTGCCCAGGTTGGTAATAGCGGAGTT GAAACGGTTCTGTACGGAGGAGGAG*TTATCGCCG TCTTTGATATAGCC* 3' (SEQ ID NO: 26) |
| fliC cCD154 up reverse | fliC-cCD154/loop 9 down | 5'CCAACCTGGGCAACACCTCCTCCTCC TGGATGACCACCTCCTATGCGCCGACCTCCTCCT CCTCCATTT*CCCGTTATGCCGCAGC* 3' (SEQ ID NO: 27) |
| lam 3f | outer regions of loop 9: sequencing | 5'GCCATCTCGCTTGGTGATAA 3' (SEQ ID NO: 28) |
| lam 3r | | 5'CGCTGGTATTTTGCGGTACA 3' (SEQ ID NO: 29) |

In Table 1, italicized nucleotides are complementary to either side of the lamB gene loop 9 insertion site, which corresponds to nucleotide 1257 using *S. typhimurium* as an annotated reference genome. Bold font nucleotides represent the I-SceI recognition site in the Km-f primer.

Electroporation

Transformation of pKD46 into *S. enteritidis* was the first step carried out so that Red recombinase enzymes could be used for mediating recombination of subsequent mutations. Plasmid pKD46 was harvested from *E. coli* BW25113 (Datsenko and Wanner, PNAS 2000, 97:6640-6645) using a plasmid preparation kit (Qiagen Valencia, Calif., USA). Then 0.5 µL of pKD46 DNA was used for transformation into *S. enteritidis* 13A which had been prepared for electroporation. (Datsenko and Wanner, PNAS 2000, 97:6640-6645). Briefly, cells were inoculated into 10-15 mL of 2×YT broth and grown at 37° C. overnight. Then 100 µL of overnight culture was re-inoculated into 10 mL fresh 2×YT broth at 37° C. for 3-4 hours. Cells to be transformed with pKD46 plasmid were heated at 50° C. for 25 minutes to help inactivate host restriction. Cells were washed five times in ddH$_2$O water and resuspended in 60 µL of 10% glycerol. Cells were then pulsed at 2400-2450 kV for 1-6 ms, incubated in SOC for 2-3 hours at 30° C. and plated on LB media with appropriate antibiotics. *S. enteritidis* transformants with pKD46 were maintained at 30° C. When these transformants were prepared for additional electroporation reactions, all steps were the same except that 15% arabinose was added to induce Red recombinase enzymes one hour prior to washing, and cells did not undergo the 50° C. heat step.

Loop 9 up-I-SceI/Km^r-Loop 9 Down Construct

Figure 2A:
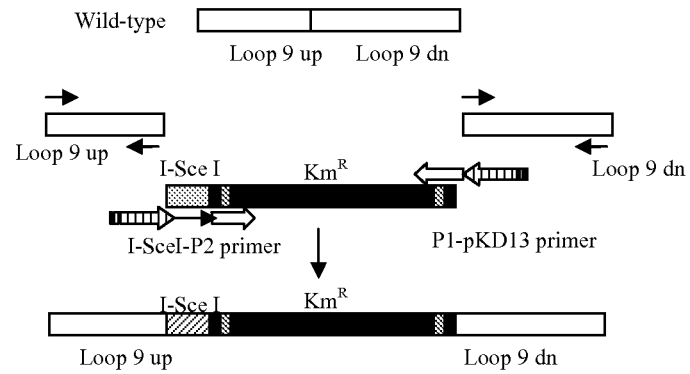
FIG. 2 depicts the design scheme of the overlapping extension PCR method used to generate the fliC and fliC-CD154 insertions into loop 9 of the lamB polynucleotide.

Introduction of I-SceI enzyme recognition site along with the Km^r gene into loop 9 of the lamB gene was done by combining the Red recombinase system (Datsenko and Wanner, PNAS 2000, 97:6640-6645, which is incorporated herein by reference in its entirety) and overlapping PCR (Horton et al., BioTechniques 1990, 8:528-535, which is incorporated herein by reference in its entirety). The insertion site corresponds to nucleotide 1257 of the lamB gene using *Salmonella typhimurium* LT2 (*S. typhimurium*) as an annotated reference genome. First, the upstream and downstream regions immediately flanking the loop 9 insertion site (loop 9 up and loop 9 down, respectively) were amplified separately. Primers used were lam-up-f and lam-up-r for loop 9 up and lam-dn-f and lam-dn-r for loop 9 down. Then the Km$^r$ gene from pKD13 plasmid was amplified using primers Km-f and Km-r. Here, the I-SceI enzyme site was synthetically added to the 5' end of Km-f primer then preceded by a region complimentary to the loop-up-r primer. Likewise, a region complimentary to the loop-dn-f primer was added to the 5' end of Km-r primer. The complimentary regions allow all 3 PCR products to anneal when used as templates in one PCR reaction. FIG. 2a represents this design scheme. PCR fragments consisting of loop 9 up-I-SceI/Km$^r$-loop 9 down sequence (PCR-A) were electroporated into S. enteritidis cells, which harbored pKD46 and were induced by arabinose, and then plated on LB with Km plates. To verify the correct sequence orientation of the mutation, we performed colony PCR with primer pairs Kan4F/lam3f and Kan4R/lam3r, where Kan4F and Kan4R are Km$^r$ gene-specific primers and lam3f and lam3r are primers located outside the lamB loop 9 region. These PCR fragments were gel purified (Qiagen, Valencia, Calif., USA) and used for DNA sequencing.

Loop 9 up-fliC or CD154s or Combination Sequence-Loop 9 Down Construct

Figure 2B:
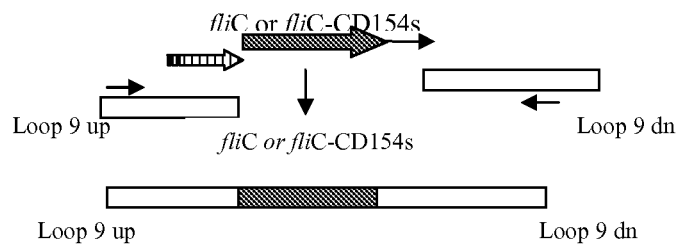
Figure 3:
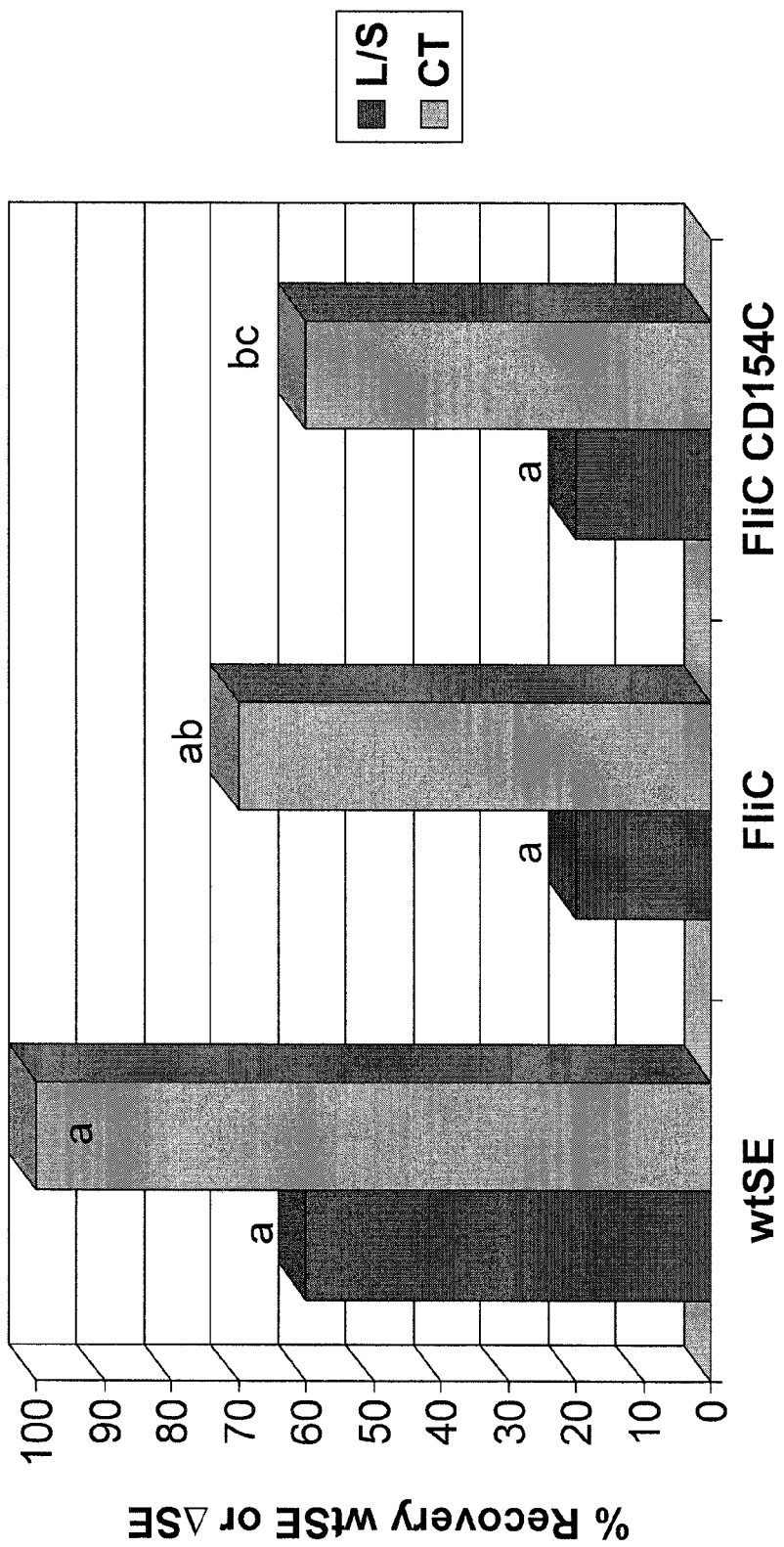
FIG. 3 is a bar graph showing the percent *Salmonella enteritidis* recovery as compared to the initial inoculum in the liver/spleen and cecal tonsils at 3 days post-inoculation with the indicated bacteria.

The final overlapping PCR fragment, PCR-B, contained the added fliC antigen (or combination with CD154 sequences flanked by loop 9 up and down regions (FIG. 2b). Combination sequences consisted of fliC polynucleotide comprising SEQ ID NO:1 and a CD154 polynucleotide sequence along with spacers such as Glycine (Gly) or Serine (Ser) residues.

To shorten the amount of steps for construction of the next fragment, the fliC or fliC-CD154 sequence was synthetically added to the 5' end of the lam-dn-f primer and preceded by the complimentary region to the loop-up-r primer. The previously used PCR product for loop 9 up could be used together with the newly constructed PCR product in which fliC or fliC-CD154 were incorporated at the 5' end of loop 9 down to perform the final PCR reaction. However, for other insert sequences (referred to as combination sequences), an extra PCR step was needed, due to the longer lengths of insert sequences, to amplify loop 9 up with added nucleotides specific to insertion sequences connected to loop-up-r primer. The coding sequence for Gly (GGT) and Serine (TCC) as well as all other amino acids were chosen based on compiled data of the most frequently used codons in *E. coli* and *Salmonella typhimurium* proteins. See Table 1 for further details of primer design.

Genomic Replacement of I-SceI/$Km^r$ with fliC or fliC-CD154

PCR-B products were electroporated into *S. enteritidis* cells along with plasmid pBC-I-SceI at a molar ratio of approximately 40:1 (Kang et al., J Bacteriol 2004, 186:4921-4930, which is incorporated herein by reference in its entirety). Clones for each PCR-B recombination mutation were chosen according to the ability to grow on Cm plates but not on Km plates, due to the replacement of PCR-B for the $Km^r$ encoding PCR-A sequence. Modified regions in the selected clones were PCR-amplified, and DNA sequences were determined using primers lam3f and lam3r located outside the loop 9 down and up amplified regions.

I-SceI site/$Km^r$ Insertion Mutation

The first mutation step involved designing a PCR fragment, PCR-A, which would serve as the carrier of the I-SceI site/$Km^r$ cassette to be inserted into the lamB site. PCR-A consisted of the I-SceI enzyme recognition site adjacent to the $Km^r$ gene with approximately 200-300 bp of flanking DNA on each end homologous to the upstream and downstream regions of lamB loop 9 insertion site (loop 9 up and loop 9 down, respectively). The fragment was introduced into *S. enteritidis* cells expressing Red recombinase enzymes and $Km^r$ colonies were selected. After screening a few colonies by colony PCR, positive clones were sequenced for the desired inserted I-SceI site/$Km^r$ sequence, and the identified mutant was selected and designated as SE164.

Genomic Replacement of I-SceI/$Km^r$ with fliC or fliC-CD154

The second mutation step required constructing a PCR fragment, referred to as PCR-B and shown in FIG. 2B, consisting of the final insertion sequence, fliC or fliC-CD154, flanked by lamB homologous fragments. PCR-B amplicons have no selection marker and must be counter-selected after replacement for the previous I-SceI site/$Km^r$ mutation in SE164. Plasmid pBC-I-SceI encodes the $Cm^r$ gene and the I-SceI enzyme, which will cut the genome at the I-SceI site of SE164. Therefore, pBC-I-SceI was electroporated into SE164 along with PCR-B. After recombination of PCR-B to replace PCR-A, positive clones were chosen based on the ability to grow on Cm but not on Km. After DNA sequencing of mutants to confirm successful recombination of PCR-B, the strains were designated fliC, fliC-cCD154 and fliC-hCD154. Ten random clones for each the fliC and fliC-CD154 insertion were used for PCR with lam 3f and lam 3r then digested using unique restriction enzymes sites for each insertion sequence and 100% of clones tested by digestion were positive for the desired mutation sequence. Sequencing results demonstrated that the insertion of fliC or fliC-CD154 was exactly into the loop 9 region without the addition of extraneous nucleotides.

Example 2

Attenuation of fliC or fliC-CD154 Mutants/Inserts

Attenuation of SE13A was achieved by deletion mutation of the aroA gene and/or the htrA gene. Mutation of the aroA gene, a key gene in the chorismic acid pathway of bacteria, results in a severe metabolic deficiency which affects seven separate biochemical pathways. Mutation of the htrA gene reduces the cell's ability to withstand exposure to low and high temperatures, low pH, and oxidative and DNA damaging agents and reduces the bacteria's virulence.

To achieve deletion mutations in SE13A, the target gene sequence in the bacterial genome of *S. enteritidis* was replaced with the Km resistant gene sequence. This was completed using overlapping extension PCR and electroporation of the PCR products as described above. The Km resistance gene was targeted into the genomic region containing the genes of interest (aroA or htrA) by flanking the Km resistance gene with 200-300 base pairs of sequences homologous to the genes of interest. Once Km resistant mutants were obtained, the aroA or htrA deletion mutations were confirmed by DNA sequencing. The attenuated strains were also tested in vivo with regards to clearance time. Both of the attenuated strains had quicker clearance times than did the wildtype 13A strain, but both were able to colonize the liver, spleen, and cecal tonsils of chickens after oral infection. In addition, an attenuated strain lacking both aroA and htrA was also isolated.

Example 3

Colonization of Chickens

Day-of-hatch chicks (40 per group) were inoculated with about $1\times10^8$ cfu of various *Salmonella* isolates or saline control. The *Salmonella* isolates included the following: wtSE represents the original field isolate of *Salmonella enteritidis* 13A (SE13A); fliC represents the double attenuated (i.e., aroA and htrA) wild type SE13A expressing fliC in the lamB loop (cell surface); fliC-CD154C represents the double attenuated wild type SE13A similarly expressing fliC and a chicken CD154 oligopeptide.

On days 3 and 21 post-vaccination the cecal tonsils (CT) and the liver and spleen (L/S) were harvested and bacterial recovery assessed by a standard colony forming unit (cfu) assay in 10 animals per group. The results are shown in FIG. 3 (Day 3) and FIG. 4 (Day 21) and are reported as Percent wtSE recovery as measured by the number of cfu recovered compared to the inoculum. No (zero) Salmonellae were recovered from either the non-challenged controls (control) at day 3 or day 21 post-vaccination or the chicks inoculated with the fliC mutant by day 21 post-vaccination in the liver or spleen. These results suggest that the chicks are mounting an effective immune response against the fliC antigen that allows them to clear the vaccine strain more rapidly than the wild-type SE13A. Different letters on the top of the bars in the graphs are indicative of significant differences from the wtSE ($p<0.05$). Therefore expression of fliC polypeptide on the surface of the bacterium induces a more robust immune response. Similar results were obtained when a human CD154 oligopeptide was used in place of the chicken CD154 peptide.

Serum was collected from the inoculated chicks and fliC specific antibody was measured by ELISA using standard procedures. FliC antibody production was not significantly increased in the animals vaccinated with fliC or fliC-CD154 containing SE.

We claim:

1. A bacterial vaccine vector comprising a first polynucleotide sequence encoding a fliC polypeptide and a second polynucleotide sequence encoding a CD154 polypeptide capable of binding CD40, the CD154 polypeptide having fewer than 50 amino acids and comprising amino acids 140-149 of SEQ ID NO: 8, or at least one of SEQ ID NO: 3, SEQ ID NO: 4, SEQ ID NO: 5, SEQ ID NO: 6, and SEQ ID NO: 7, wherein the fliC polypeptide is encoded by an exogenous polynucleotide and consists of SEQ ID NO: 1, SEQ ID NO: 2, or SEQ ID NO: 12 and wherein each of the first polynucleotide and the second polynucleotide are inserted into a polynucleotide sequence encoding an external portion of a transmembrane protein such that the fliC polypeptide and the CD154 polypeptide are expressed on the surface of the vaccine vector.

2. The vaccine vector of claim 1, wherein the bacterium is selected from the group consisting of *Salmonella* species, *Escherichia* species, *Bacillus* species and *Lactobacillus* species.

3. The vaccine vector of claim 1, wherein the vaccine comprises more than one copy of the first polynucleotide sequence.

4. The vaccine vector of claim 1, wherein the vaccine comprises more than one copy of the second polynucleotide sequence.

5. The vaccine vector of claim 1, wherein the first polynucleotide sequence is linked in frame to the second polynucleotide sequence.

6. A vaccine vector comprising a variant of *Salmonella enteritidis* 13A, wherein the *Salmonella* comprises an exogenous first polynucleotide sequence encoding a fliC polypeptide and a second polynucleotide sequence encoding a CD154 polypeptide capable of binding CD40, the CD154 polypeptide having fewer than 50 amino acids and comprising amino acids 140-149 of SEQ ID NO: 8, or at least one of SEQ ID NO: 3, SEQ ID NO: 4, SEQ ID NO: 5, SEQ ID NO 6, and SEQ ID NO: 7, wherein the fliC polypeptide is encoded by an exogenous polynucleotide and consists of SEQ ID NO: 1, SEQ ID NO: 2, or SEQ ID NO: 12 and wherein each of the first polynucleotide and the second polynucleotide are inserted into a polynucleotide sequence encoding an external portion of a transmembrane protein such that the fliC polypeptide and the CD154 polypeptide are expressed on the surface of the vaccine vector.

7. A method of enhancing the immune response against a flagellated bacterium in a subject comprising administering to the subject the bacterial vaccine vector of claim 1 in an amount effective to enhance the immune response of the subject to the flagellated bacterium.

8. The method of claim 7, wherein the bacterium is selected from the group consisting of *Salmonella* species, *Escherichia* species, *Bacillus* species and *Lactobacillus* species.

9. The method of claim 7, wherein the bacterium is administered by a method selected from the group consisting of oral, intranasal, parenteral, and in ovo.

10. The method of claim 7, wherein the enhanced immune response comprises an enhanced antibody response or an enhanced T cell response.

11. The method of claim 7, wherein the subject is a member of a poultry species or a mammal.

12. The method of claim 7, wherein the bacterium is killed prior to administration to the subject.

13. The method of claim 7, wherein the bacterium is not capable of replicating in the subject.

14. The vaccine vector of claim 1, wherein the bacterial vaccine vector is *Salmonella* or *Bacillus*.

15. The vaccine vector of claim 1, wherein the transmembrane protein is LamB.

16. The vaccine vector of claim 1, wherein the bacterial vaccine vector is killed or not capable of replication.

17. The vaccine vector of claim 6, wherein the transmembrane protein is LamB.

18. The vaccine vector of claim 6, wherein the bacterial vaccine vector is killed or not capable of replication.

* * * * *

SEQUENCE LISTING

```
<160> NUMBER OF SEQ ID NOS: 29

<210> SEQ ID NO 1
<211> LENGTH: 7
<212> TYPE: PRT
<213> ORGANISM: Salmonella enteritidis

<400> SEQUENCE: 1

Ser Ala Ile Thr Asn Leu Gly
1               5

<210> SEQ ID NO 2
<211> LENGTH: 7
<212> TYPE: PRT
<213> ORGANISM: Escherichia coli

<400> SEQUENCE: 2

Ser Ala Val Thr Asn Leu Asn
1               5

<210> SEQ ID NO 3
<211> LENGTH: 11
<212> TYPE: PRT
<213> ORGANISM: Homo sapiens

<400> SEQUENCE: 3

Trp Ala Glu Lys Gly Tyr Tyr Thr Met Ser Cys
1               5                   10

<210> SEQ ID NO 4
<211> LENGTH: 11
<212> TYPE: PRT
<213> ORGANISM: Gallus gallus

<400> SEQUENCE: 4

Trp Met Thr Thr Ser Tyr Ala Pro Thr Ser Ser
1               5                   10

<210> SEQ ID NO 5
<211> LENGTH: 10
<212> TYPE: PRT
<213> ORGANISM: Anas sp.

<400> SEQUENCE: 5

Trp Asn Lys Thr Ser Tyr Ala Pro Met Asn
1               5                   10
```

<210> SEQ ID NO 6
<211> LENGTH: 10
<212> TYPE: PRT
<213> ORGANISM: Mus sp.

<400> SEQUENCE: 6

Trp Ala Lys Lys Gly Tyr Tyr Thr Met Lys
1               5                   10

<210> SEQ ID NO 7
<211> LENGTH: 10
<212> TYPE: PRT
<213> ORGANISM: Bos taurus

<400> SEQUENCE: 7

Trp Ala Pro Lys Gly Tyr Tyr Thr Leu Ser
1               5                   10

<210> SEQ ID NO 8
<211> LENGTH: 261
<212> TYPE: PRT
<213> ORGANISM: Homo sapiens

<400> SEQUENCE: 8

Met Ile Glu Thr Tyr Asn Gln Thr Ser Pro Arg Ser Ala Ala Thr Gly
1               5                   10                  15

Leu Pro Ile Ser Met Lys Ile Phe Met Tyr Leu Leu Thr Val Phe Leu
                20                  25                  30

Ile Thr Gln Met Ile Gly Ser Ala Leu Phe Ala Val Tyr Leu His Arg
            35                  40                  45

Arg Leu Asp Lys Ile Glu Asp Glu Arg Asn Leu His Glu Asp Phe Val
        50                  55                  60

Phe Met Lys Thr Ile Gln Arg Cys Asn Thr Gly Glu Arg Ser Leu Ser
65                  70                  75                  80

Leu Leu Asn Cys Glu Glu Ile Lys Ser Gln Phe Glu Gly Phe Val Lys
                85                  90                  95

Asp Ile Met Leu Asn Lys Glu Glu Thr Lys Lys Glu Asn Ser Phe Glu
            100                 105                 110

Met Gln Lys Gly Asp Gln Asn Pro Gln Ile Ala Ala His Val Ile Ser
        115                 120                 125

Glu Ala Ser Ser Lys Thr Thr Ser Val Leu Gln Trp Ala Glu Lys Gly
130                 135                 140

Tyr Tyr Thr Met Ser Asn Asn Leu Val Thr Leu Glu Asn Gly Lys Gln
145                 150                 155                 160

Leu Thr Val Lys Arg Gln Gly Leu Tyr Tyr Ile Tyr Ala Gln Val Thr
                165                 170                 175

Phe Cys Ser Asn Arg Glu Ala Ser Ser Gln Ala Pro Phe Ile Ala Ser
            180                 185                 190

Leu Cys Leu Lys Ser Pro Gly Arg Phe Glu Arg Ile Leu Leu Arg Ala
        195                 200                 205

Ala Asn Thr His Ser Ser Ala Lys Pro Cys Gly Gln Gln Ser Ile His
210                 215                 220

Leu Gly Gly Val Phe Glu Leu Gln Pro Gly Ala Ser Val Phe Val Asn
225                 230                 235                 240

Val Thr Asp Pro Ser Gln Val Ser His Gly Thr Gly Phe Thr Ser Phe
                245                 250                 255

Gly Leu Leu Lys Leu
            260

<210> SEQ ID NO 9
<211> LENGTH: 272
<212> TYPE: PRT
<213> ORGANISM: Gallus gallus

<400> SEQUENCE: 9

Met Asn Glu Ala Tyr Ser Pro Ala Ala Pro Arg Pro Met Gly Ser Thr
1               5                   10                  15

Ser Pro Ser Thr Met Lys Met Phe Met Cys Phe Leu Ser Val Phe Met
            20                  25                  30

Val Val Gln Thr Ile Gly Thr Val Leu Phe Cys Leu Tyr Leu His Met
        35                  40                  45

Lys Met Asp Lys Met Glu Glu Val Leu Ser Leu Asn Glu Asp Tyr Ile
    50                  55                  60

Phe Leu Arg Lys Val Gln Lys Cys Gln Thr Gly Glu Asp Gln Lys Ser
65                  70                  75                  80

Thr Leu Leu Asp Cys Gly Lys Val Leu Lys Gly Phe Gln Asp Leu Gln
                85                  90                  95

Cys Lys Asp Arg Thr Ala Ser Glu Glu Leu Pro Lys Phe Glu Met His
            100                 105                 110

Arg Gly His Glu His Pro His Leu Lys Ser Arg Asn Glu Thr Ser Val
        115                 120                 125

Ala Glu Glu Lys Arg Gln Pro Ile Ala Thr His Leu Ala Gly Val Lys
    130                 135                 140

Ser Asn Thr Thr Val Arg Val Leu Lys Trp Met Thr Thr Ser Tyr Ala
145                 150                 155                 160

Pro Thr Ser Ser Leu Ile Ser Tyr His Glu Gly Lys Leu Lys Val Glu
                165                 170                 175

Lys Ala Gly Leu Tyr Tyr Ile Tyr Ser Gln Val Ser Phe Cys Thr Lys
            180                 185                 190

Ala Ala Ala Ser Ala Pro Phe Thr Leu Tyr Ile Tyr Leu Tyr Leu Pro
        195                 200                 205

Met Glu Glu Asp Arg Leu Leu Met Lys Gly Leu Asp Thr His Ser Thr
    210                 215                 220

Ser Thr Ala Leu Cys Glu Leu Gln Ser Ile Arg Glu Gly Gly Val Phe
225                 230                 235                 240

Glu Leu Arg Gln Gly Asp Met Val Phe Val Asn Val Thr Asp Ser Thr
                245                 250                 255

Ala Val Asn Val Asn Pro Gly Asn Thr Tyr Phe Gly Met Phe Lys Leu
            260                 265                 270

<210> SEQ ID NO 10
<211> LENGTH: 15
<212> TYPE: PRT
<213> ORGANISM: Salmonella enteritidis

<400> SEQUENCE: 10

Val Gln Asn Arg Phe Asn Ser Ala Ile Thr Asn Gly Leu Asn Thr
1               5                   10                  15

<210> SEQ ID NO 11
<211> LENGTH: 15
<212> TYPE: PRT
<213> ORGANISM: Salmonella enteritidis

<400> SEQUENCE: 11

```
Gly Ala Val Gln Asn Arg Phe Asn Ser Ala Ile Thr Leu Asn Gly
1               5                   10                  15
```

<210> SEQ ID NO 12
<211> LENGTH: 13
<212> TYPE: PRT
<213> ORGANISM: Salmonella enteritidis

<400> SEQUENCE: 12

```
Ile Gln Asn Arg Phe Asp Ser Ala Ile Thr Leu Asn Gly
1               5                   10
```

<210> SEQ ID NO 13
<211> LENGTH: 18
<212> TYPE: DNA
<213> ORGANISM: Artificial Sequence
<220> FEATURE:
<223> OTHER INFORMATION: I-SceI enzyme recognition sequence

<400> SEQUENCE: 13
tagggataac agggtaat                                                   18

<210> SEQ ID NO 14
<211> LENGTH: 20
<212> TYPE: DNA
<213> ORGANISM: Artificial Sequence
<220> FEATURE:
<223> OTHER INFORMATION: loop 9 up

<400> SEQUENCE: 14
tgtacaagtg gacgccaatc                                                 20

<210> SEQ ID NO 15
<211> LENGTH: 24
<212> TYPE: DNA
<213> ORGANISM: Artificial Sequence
<220> FEATURE:
<223> OTHER INFORMATION: loop 9 up

<400> SEQUENCE: 15
gttatcgccg tctttgatat agcc                                            24

<210> SEQ ID NO 16
<211> LENGTH: 20
<212> TYPE: DNA
<213> ORGANISM: Artificial Sequence
<220> FEATURE:
<223> OTHER INFORMATION: loop 9 down

<400> SEQUENCE: 16
atttcccgtt atgccgcagc                                                 20

<210> SEQ ID NO 17
<211> LENGTH: 20
<212> TYPE: DNA
<213> ORGANISM: Artificial Sequence
<220> FEATURE:
<223> OTHER INFORMATION: loop 9 down

<400> SEQUENCE: 17
gttaaacaga gggcgacgag                                                 20

<210> SEQ ID NO 18
<211> LENGTH: 68
<212> TYPE: DNA
<213> ORGANISM: Artificial Sequence

```
<220> FEATURE:
<223> OTHER INFORMATION: I-SceI/Kmr gene

<400> SEQUENCE: 18
gctatatcaa agacggcgat aactaactat aacggtccta aggtagcgaa tttccgggga    60
tccgtcga                                                            68

<210> SEQ ID NO 19
<211> LENGTH: 40
<212> TYPE: DNA
<213> ORGANISM: Artificial Sequence
<220> FEATURE:
<223> OTHER INFORMATION: I-SceI/Kmr gene

<400> SEQUENCE: 19
gctgcggcat aacgggaaat tgtaggctgg agctgcttcg                          40

<210> SEQ ID NO 20
<211> LENGTH: 20
<212> TYPE: DNA
<213> ORGANISM: Artificial Sequence
<220> FEATURE:
<223> OTHER INFORMATION: inside Kmr gene: sequencing

<400> SEQUENCE: 20
caaaagcgct ctgaagttcc                                                20

<210> SEQ ID NO 21
<211> LENGTH: 20
<212> TYPE: DNA
<213> ORGANISM: Artificial Sequence
<220> FEATURE:
<223> OTHER INFORMATION: inside Kmr gene: sequencing

<400> SEQUENCE: 21
gcgtgagggg atcttgaagt                                                20

<210> SEQ ID NO 22
<211> LENGTH: 44
<212> TYPE: DNA
<213> ORGANISM: Artificial Sequence
<220> FEATURE:
<223> OTHER INFORMATION: fliC/ loop 9 up

<400> SEQUENCE: 22
cggttctgta cggaggagga gttatcgccg tctttgatat agcc                     44

<210> SEQ ID NO 23
<211> LENGTH: 83
<212> TYPE: DNA
<213> ORGANISM: Artificial Sequence
<220> FEATURE:
<223> OTHER INFORMATION: fliC/ loop 9 down

<400> SEQUENCE: 23
tcctcctccg tacagaaccg tttcaactcc gctattacca acctgggcaa cacctcctcc    60
tccatttccc gttatgccgc agc                                            83

<210> SEQ ID NO 24
<211> LENGTH: 81
<212> TYPE: DNA
<213> ORGANISM: Artificial Sequence
<220> FEATURE:
<223> OTHER INFORMATION: fliC-hCD154/ loop 9 up
```

```
<400> SEQUENCE: 24
ggaggtgttg cccaggttgg taatagcgga gttgaaacgg ttctgtacgg aggaggagtt      60
atcgccgtct ttgatatagc c                                                81

<210> SEQ ID NO 25
<211> LENGTH: 85
<212> TYPE: DNA
<213> ORGANISM: Artificial Sequence
<220> FEATURE:
<223> OTHER INFORMATION: fliC-hCD154/ loop 9 down

<400> SEQUENCE: 25
ccaacctggg caacacctcc tcctcctggg cagaaaaagg ttattatacc atgtcttcct      60
cctccatttc ccgttatgcc gcagc                                            85

<210> SEQ ID NO 26
<211> LENGTH: 81
<212> TYPE: DNA
<213> ORGANISM: Artificial Sequence
<220> FEATURE:
<223> OTHER INFORMATION: fliC-cCD154/ loop 9 up

<400> SEQUENCE: 26
ggaggtgttg cccaggttgg taatagcgga gttgaaacgg ttctgtacgg aggaggagtt      60
atcgccgtct ttgatatagc c                                                81

<210> SEQ ID NO 27
<211> LENGTH: 85
<212> TYPE: DNA
<213> ORGANISM: Artificial Sequence
<220> FEATURE:
<223> OTHER INFORMATION: fliC-cCD154/ loop 9 down

<400> SEQUENCE: 27
ccaacctggg caacacctcc tcctcctgga tgaccacctc ctatgcgccg acctcctcct      60
cctccatttc ccgttatgcc gcagc                                            85

<210> SEQ ID NO 28
<211> LENGTH: 20
<212> TYPE: DNA
<213> ORGANISM: Artificial Sequence
<220> FEATURE:
<223> OTHER INFORMATION: outer regions of loop 9: sequencing

<400> SEQUENCE: 28
gccatctcgc ttggtgataa                                                  20

<210> SEQ ID NO 29
<211> LENGTH: 20
<212> TYPE: DNA
<213> ORGANISM: Artificial Sequence
<220> FEATURE:
<223> OTHER INFORMATION: outer regions of loop 9: sequencing

<400> SEQUENCE: 29
cgctggtatt ttgcggtaca                                                  20
```